US012752029B2

(12) United States Patent
Naidis et al.

(10) Patent No.: US 12,752,029 B2
(45) Date of Patent: Oct. 6, 2026

(54) TECHNIQUES FOR OLFACTORY TRAINING USING SCENT DISPENSING DEVICES

(71) Applicant: iRoma Scents A.B. Ltd., Herzliya (IL)

(72) Inventors: Eugene Naidis, Ashkelon (IL); Avner Gal, Herzliya (IL)

(73) Assignee: iRoma Scents A.B. Ltd., Herzliya (IL)

( * ) Notice: Subject to any disclaimer, the term of this patent is extended or adjusted under 35 U.S.C. 154(b) by 0 days.

(21) Appl. No.: 18/917,458

(22) Filed: Oct. 16, 2024

(65) Prior Publication Data

US 2025/0121111 A1 Apr. 17, 2025

Related U.S. Application Data

(60) Provisional application No. 63/590,910, filed on Oct. 17, 2023.

(51) Int. Cl.
*A61L 9/04* (2006.01)
*A61B 5/00* (2006.01)
(Continued)

(52) U.S. Cl.
CPC .............. *A61L 9/04* (2013.01); *A61B 5/4011* (2013.01); *A61L 9/14* (2013.01); *G09B 19/00* (2013.01); *A61L 2209/13* (2013.01)

(58) Field of Classification Search
CPC .......... A61L 9/037; A61L 9/035; A61L 9/125; A61L 2209/111; A61L 2209/133; A61L 2209/134; A61L 9/14; A61L 9/03; A61L 9/122; B05B 7/2491; B05B 7/2497; B05B 11/0054; B05B 11/0078; B05B 12/08; B05B 1/005; B05B 12/1409; B05B 15/55;
(Continued)

(56) References Cited

U.S. PATENT DOCUMENTS

| | | | | |
|---|---|---|---|---|
| 6,558,322 | B1 * | 5/2003 | Busch ................ | G01N 33/0001 600/303 |
| 11,103,178 | B1 | 8/2021 | Buckler et al. | |

(Continued)

FOREIGN PATENT DOCUMENTS

| | | | |
|---|---|---|---|
| KR | 20100050120 | A1 | 5/2010 |
| KR | 20190094900 | A | 8/2019 |

(Continued)

OTHER PUBLICATIONS

International Search Report for PCT/IB2024/060158, dated Dec. 9, 2024. Searching Authority, Israel Patent Office, Jerusalem, Israel.

(Continued)

*Primary Examiner* — Jennifer Robertson
*Assistant Examiner* — Elina Sohyun Jang
(74) *Attorney, Agent, or Firm* — M&B IP Analysts, LLC

(57) ABSTRACT

A system and method for olfactory training using scent dispensing devices. A method includes determining olfactory training inputs; generating training exercise data, wherein the training exercise data includes instructions for dispensing scents; causing the execution of the training exercises by at least dispensing scents via a scent dispensing device; obtaining training results data based on user inputs received during the training exercise; and determining a plan for a next stage of training based on the training results data.

19 Claims, 13 Drawing Sheets

(51) Int. Cl.
*A61L 9/14* (2006.01)
*G09B 19/00* (2006.01)

(58) Field of Classification Search
CPC ........... A61M 11/04; A61M 2205/3334; A24F 40/30; A24F 40/42; A24F 40/485; A24F 40/60; A24F 40/48; A24F 40/10; A24F 40/50; A24F 7/00; A24F 40/20; A24F 40/40; A24F 40/51; A61K 31/05; A24B 15/301; A24B 15/303; H02M 1/0003; F24F 6/08; Y10S 261/65; Y10T 74/14; Y10T 74/1412; Y10T 74/1418
See application file for complete search history.

(56) References Cited

U.S. PATENT DOCUMENTS

2016/0107186 A1 4/2016 Chao et al.
2016/0379506 A1* 12/2016 Okada .................... G09B 19/00 434/236
2021/0170060 A1* 6/2021 Galvão ..................... A61L 9/14
2021/0298661 A1 9/2021 Smith et al.
2022/0202607 A1* 6/2022 Azoulay ............... A61M 15/08

FOREIGN PATENT DOCUMENTS

KR 20200061246 A 6/2020
KR 20230068857 A 5/2023
WO 2011021980 A1 2/2011
WO 2020060167 A1 3/2020
WO 2023119275 A1 6/2023

OTHER PUBLICATIONS

Written Opinion of the Searching Authority for PCT/IB2024/060158, dated Dec. 9, 2024. Searching Authority, Israel Patent Office, Jerusalem, Israel.

* cited by examiner

FIG. 6C
600C
Level Five
What scent did you smell? Take your time and answer
Banana AROMA
Chocolate AROMA
Scent it again
I don't know
Exit game
Step 1
Step 2
Step 3
Step 4
Step 5
Finish

FIG. 6D
600D
Level Five
What scent did you smell? Take your time and answer
Banana AROMA
Chocolate
Next
Exit game
Step 1
Step 2
Step 3
Step 4
Step 5
Finish

TECHNIQUES FOR OLFACTORY TRAINING USING SCENT DISPENSING DEVICES

CROSS-REFERENCE TO RELATED APPLICATIONS

This application claims the benefit of U.S. Provisional Patent Application No. 63/590,910 filed on Oct. 17, 2023. This application also relates to PCT Application No. PCT/IL2022/051351 filed on Dec. 20, 2022, which claims the benefit of U.S. Provisional Patent Application No. 63/265,729 filed on Dec. 20, 2021.

The contents of the above-noted applications are hereby incorporated by reference.

TECHNICAL FIELD

The present disclosure relates generally to olfactory training, and more specifically to olfactory training utilizing scent dispensing devices.

BACKGROUND

Anosmia and hyposmia are conditions in which a subject loses or experiences reduced sense of smell. The condition can occur for various reasons such as, but not limited to, viral infections, head injuries, sinus issues, and neurological disorders. Around 2020, certain variants of the COVID-19 variant of SARS-COV-2 caused many individuals to experience temporary or longer-term losses of sense or smell.

There are different approaches to treating anosmia such as surgical interventions, medications, lifestyle changes, supportive care, and olfactory training. Surgical and medication solutions face many potential downsides including risk of harm or side effects, and are therefore undesirable if other options are available. Other solutions requiring altering lifestyle or seeking additional support may also be undesirable, particularly long term.

Existing solutions for olfactory training typically involve regular exposure to a variety of strongly scented substances, like essential oils, in order to stimulate and retrain the olfactory nerves. A major challenge of these solutions is the reliance on consistency by the subject undergoing olfactory training. Establishing and maintaining an olfactory training routine can be particularly challenging due to the mundane and repetitive nature of existing olfactory testing, especially for younger subjects or subjects that would otherwise have difficulty maintaining attention to such tasks. Even when a consistent schedule is maintained, inconsistency in how the test is conducted can lead to suboptimal results.

It would therefore be advantageous to provide a solution that would overcome the challenges noted above.

SUMMARY

A summary of several example embodiments of the disclosure follows. This summary is provided for the convenience of the reader to provide a basic understanding of such embodiments and does not wholly define the breadth of the disclosure. This summary is not an extensive overview of all contemplated embodiments, and is intended to neither identify key or critical elements of all embodiments nor to delineate the scope of any or all aspects. Its sole purpose is to present some concepts of one or more embodiments in a simplified form as a prelude to the more detailed description that is presented later. For convenience, the term "some embodiments" or "certain embodiments" may be used herein to refer to a single embodiment or multiple embodiments of the disclosure.

Certain embodiments disclosed herein include a method for olfactory training. The method comprises: generating olfactory training exercise data based on inputs indicating a plurality of scents to be dispensed during a plurality of olfactory training exercises; and causing a scent dispensing device to dispense the plurality of scents based on the olfactory training exercise data, each scent of the plurality of scents being dispensed during operation of a respective olfactory training exercise of the plurality of olfactory training exercises, wherein the scent dispensing device includes a plurality of chambers, wherein each chamber of the plurality of chambers includes a respective scent essence of a plurality of scent essences, wherein dispensing each scent of the plurality of scents includes causing at least one scent essence of the plurality of scent essences to be dispensed via at least a portion of the plurality of chambers of the scent dispensing device.

Certain embodiments disclosed herein also include a non-transitory computer-readable medium having stored thereon causing a processing circuitry to execute a process, the process comprising: generating olfactory training exercise data based on inputs indicating a plurality of scents to be dispensed during a plurality of olfactory training exercises; and causing a scent dispensing device to dispense the plurality of scents based on the olfactory training exercise data, each scent of the plurality of scents being dispensed during operation of a respective olfactory training exercise of the plurality of olfactory training exercises, wherein the scent dispensing device includes a plurality of chambers, wherein each chamber of the plurality of chambers includes a respective scent essence of a plurality of scent essences, wherein dispensing each scent of the plurality of scents includes causing at least one scent essence of the plurality of scent essences to be dispensed via at least a portion of the plurality of chambers of the scent dispensing device.

Certain embodiments disclosed herein also include a system for olfactory training. The system comprises: a processing circuitry; and a memory, the memory containing instructions that, when executed by the processing circuitry, configure the system to: generate olfactory training exercise data based on inputs indicating a plurality of scents to be dispensed during a plurality of olfactory training exercises; and cause a scent dispensing device to dispense the plurality of scents based on the olfactory training exercise data, each scent of the plurality of scents being dispensed during operation of a respective olfactory training exercise of the plurality of olfactory training exercises, wherein the scent dispensing device includes a plurality of chambers, wherein each chamber of the plurality of chambers includes a respective scent essence of a plurality of scent essences, wherein dispensing each scent of the plurality of scents includes causing at least one scent essence of the plurality of scent essences to be dispensed via at least a portion of the plurality of chambers of the scent dispensing device.

Certain embodiments disclosed herein include a method for olfactory training. The method comprises: determining a plurality of scents to be dispensed during a plurality of olfactory training exercises indicated in olfactory training exercise data; and dispensing, by a scent dispensing device including a plurality of chambers, the plurality of scents based on the olfactory training exercise data, wherein dispensing each scent of the plurality of scents further comprises dispensing at least one scent essence of the plurality of scent essences via at least a portion of the plurality of chambers, wherein each chamber of the plurality of chambers includes a respective scent essence of a plurality of scent essences.

Certain embodiments disclosed herein also include a non-transitory computer-readable medium having stored thereon causing a processing circuitry to execute a process, the process comprising: determining a plurality of scents to be dispensed during a plurality of olfactory training exercises indicated in olfactory training exercise data; and dispensing, by a scent dispensing device including a plurality of chambers, the plurality of scents based on the olfactory training exercise data, wherein dispensing each scent of the plurality of scents further comprises dispensing at least one scent essence of the plurality of scent essences via at least a portion of the plurality of chambers, wherein each chamber of the plurality of chambers includes a respective scent essence of a plurality of scent essences.

Certain embodiments disclosed herein also include a system. The system comprises: a plurality of chambers, wherein each chamber of the plurality of chambers includes a respective scent essence of a plurality of scent essences; a processing circuitry; and a memory, the memory containing instructions that, when executed by the processing circuitry, configure the system to: determine a plurality of scents to be dispensed during a plurality of olfactory training exercises indicated in olfactory training exercise data; and dispense the plurality of scents based on the olfactory training exercise data, wherein dispensing each scent of the plurality of scents further comprises dispensing at least one scent essence of the plurality of scent essences via at least a portion of the plurality of chambers.

Certain embodiments disclosed herein include a method, non-transitory computer-readable medium, or system as noted above or below, wherein the olfactory training exercise data further includes an order for the plurality of olfactory training exercises, wherein the plurality of scents is dispensed according to the order.

Certain embodiments disclosed herein include a method, non-transitory computer-readable medium, or system as noted above or below, further including or being configured to perform the following step or steps: defining a plurality of exercise trigger events, each exercise trigger event corresponding to one of the plurality of scents, wherein each of the plurality of scents is dispensed at a time corresponding to occurrence of a respective exercise trigger event of the plurality of exercise trigger events.

Certain embodiments disclosed herein include a method, non-transitory computer-readable medium, or system as noted above or below, wherein the scent dispensing device is caused to dispense the plurality of scents while media content is playing, wherein each of the plurality of scents is dispensed at a time corresponding to a respective exercise trigger event of the plurality of exercise trigger events defined with respect to the media content.

Certain embodiments disclosed herein include a method, non-transitory computer-readable medium, or system as noted above or below, wherein the scent dispensing device further includes a plurality of actuators adapted to manipulate the plurality of scent essences disposed in the plurality of chambers, wherein causing the scent dispensing device to dispense the plurality of scents further includes causing the scent dispensing device to drive application of pressure in at least one actuator of the plurality of actuators in order to induce emission of the at least one scent essence of the plurality of scent essences.

Certain embodiments disclosed herein include a method, non-transitory computer-readable medium, or system as noted above or below, wherein the plurality of chambers is disposed in a drum, wherein the scent dispensing device has a housing with an aperture, wherein causing the scent dispensing device to dispense the plurality of scents further includes causing the scent dispensing device to rotate the drum in order to align at least one chamber of the plurality of chambers with the aperture.

Certain embodiments disclosed herein include a method, non-transitory computer-readable medium, or system as noted above or below, wherein causing a scent dispensing device to dispense the plurality of scents further comprises sending the olfactory training exercise data to the scent dispensing device.

Certain embodiments disclosed herein include a system as noted above or below, further comprising a plurality of actuators adapted to manipulate the plurality of scent essences disposed in the plurality of chambers; wherein the system is further configured to drive application of pressure in at least one actuator of the plurality of actuators in order to induce emission of the at least one scent essence of the plurality of scent essences.

Certain embodiments disclosed herein include a system as noted above or below, further comprising a drum, wherein the plurality of chambers is disposed in the drum; and a housing having an aperture; wherein the system is further configured to cause the drum to rotate in order to align at least one chamber of the plurality of chambers with the aperture.

Certain embodiments disclosed herein include a system as noted above or below, further comprising a plurality of actuators adapted to manipulate the plurality of scent essences disposed in the plurality of chambers; a drum, wherein the plurality of chambers is disposed in the drum; and a housing having an aperture; wherein the system is further configured to rotate the drum in at least one rotation, wherein rotating the drum at each rotation causes a chamber of the plurality of chambers to become aligned with the aperture of the housing; and drive application of pressure in at least one actuator of the plurality of actuators in order to induce emission of the at least one scent essence of the plurality of scent essences, wherein the application of pressure in each of the at least one actuator is performed during a respective rotation of the at least one rotation.

Certain embodiments disclosed herein include a system as noted above or below, wherein the olfactory training exercise data further includes an order for the plurality of olfactory training exercises, wherein the plurality of scents is dispensed according to the order, wherein the application of pressure in each of the at least one actuator is performed during a respective olfactory training exercise of the plurality of olfactory training exercises based on the order.

BRIEF DESCRIPTION OF THE DRAWINGS

The subject matter disclosed herein is particularly pointed out and distinctly claimed in the claims at the conclusion of the specification. The foregoing and other objects, features, and advantages of the disclosed embodiments will be apparent from the following detailed description taken in conjunction with the accompanying drawings.

DETAILED DESCRIPTION

Figure 1:
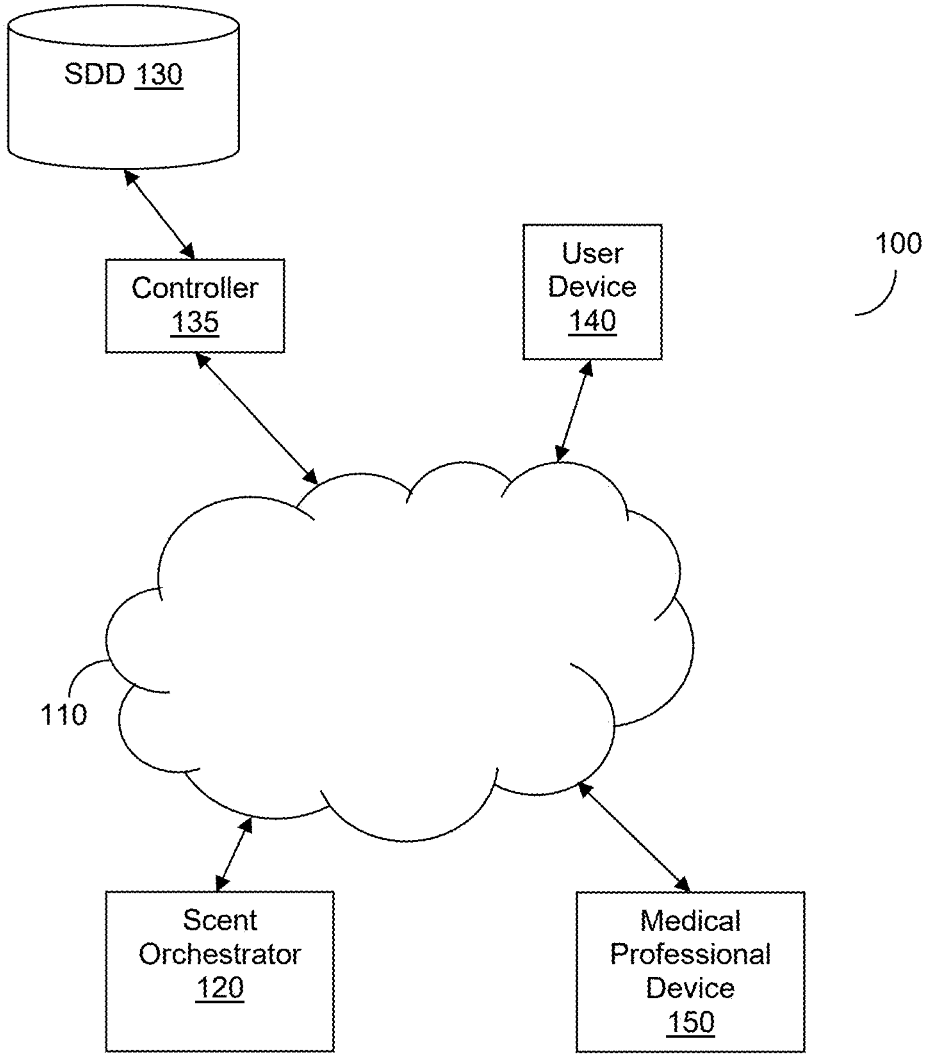
FIG. 1 is a network diagram utilized to describe various disclosed embodiments.

The various disclosed embodiments include techniques for performing olfactory training and, in particular, performing olfactory training using a scent dispensing device. Certain disclosed embodiments also include techniques for treating loss of smell such as anosmia or hyposmia via olfactory training using a scent dispensing device. Certain other embodiments further include techniques for integrating media with olfactory training.

In accordance with various disclosed embodiments, a scent dispensing device with multiple chambers is utilized. Each chamber is adapted to receive a respective scent essence or combination of scent essences such that each chamber effectively houses a respective scent. In an embodiment, each training exercise conducted by, among other things, dispensing one or more of the scents in the chamber and engaging with a user regarding the scent that was dispensed. Further, the chambers may be disposed in a multi-chamber drum having actuators adapted to manipulate the scent essence disposed in the chambers, thereby automatically causing dispensing of scents (i.e., via dispensing of scent essence from the respective chamber).

In some embodiments, the training exercises may be assisted by physical or virtual cards. The cards represent options of possible scents that the user can select from when performing the training exercises. As a non-limiting example, one card may show or say "Banana" and another card may show or say "Chocolate," and during a particular training exercise, a scent corresponding to either banana or chocolate may be dispensed before asking the user to select the scent they smelled from among the cards. The set of cards to present during a given exercise may be predetermined, prescribed by a doctor, chosen based on actions with respect to media content, adapted based on results during previous training exercises, combinations thereof, and the like.

In some embodiments, the olfactory training is integrated with media content in order to provide a more engaging user experience. To this end, in such an embodiment, training exercises are conducted during a session in which media content is presented to a user, either while the media content is being presented or during pauses in the media content. The media content may be, for example but not limited to, olfactory training exercise videos, non-olfactory training media (e.g., a movie which was not made specifically for olfactory training), combinations thereof, and the like.

In this regard, it is noted that existing solutions for olfactory training are monotonous, repetitive, and less likely for certain users to follow diligently. However, it has been identified that use of media content in combination with testing may provide ways to further engage subjects of training and, in some cases, can be used to gamify training in a manner that improves the likelihood that the subject will follow a consistent training regimen.

Additionally, using the automated scent dispensing device as described herein further improves consistency of the training exercises themselves by automating use of scents to an applicable order. When utilized in tandem with media content, scents may be deployed at an appropriate time with respect to the media content in order to effectively enhance the training. For example, a scent corresponding to an object shown in a movie may be dispensed at a time corresponding to projection of the object among the media content such as a citrus scent being dispensed when or shortly after an orange is shown in a movie. A series of scents may be defined, with scents in the series being dispensed based on trigger events which may include the passage of time, reaching a certain timestamp in a time series media content, making certain choices with respect to the media content (e.g., reaching a certain location in a video game or otherwise making certain in-game choices), and the like.

FIG. 1 shows an example network diagram 100 utilized to describe the various disclosed embodiments. In the network diagram 100, a scent orchestrator 120, a scent dispensing device (SDD) 130, a controller 135, a user device 140, and a medical professional device (MPD) 150 communicate via a network 110. The network 110 may be, but is not limited to, a wireless, cellular, or wired network, a local area network (LAN), a wide area network, a metro area network (MAN), the Internet, the worldwide web (WWW), similar networks, and any combination thereof.

The scent orchestrator 120 is configured to send instructions for scent dispensing for training exercises described herein, for example as described below with respect to FIG. 2. To this end, in an embodiment, the scent orchestrator 120 is configured to send instructions for scents to be dispensed, options to be presented, media content, trigger event definitions, the sequence or other order of training exercises, a combination thereof, and the like.

The scent dispensing device (SDD) 130 is adapted to dispense scents as part of training exercises as described herein, for example as described further below with respect to FIG. 4. In some embodiments, the SDD 130 may further include or be connected to one or more input/output devices (not shown) such as, but not limited to, a display, a touchscreen, and the like. Such input/output devices may be utilized for purposes such as, but not limited to, displaying options during training exercises, receiving user inputs of selections in response to displayed options, and the like. The SDD 130 may be an Internet of Things (IoT) device or otherwise have a network interface (not shown in FIG. 1) for communicating via the network 110.

In an embodiment, the SDD 130 has multiple chambers for receiving different scent essences, and the SDD 130 may dispense scents via ejection of scent essences from those chambers. In this regard, the SDD 130 may dispense different scents, for example according to the training exercises described herein. An example scent dispenser and drum which may be utilized for the SDD 130 is described further below with respect to FIGS. 7-8.

In some embodiments, the SDD 130 is communicatively connected to (as shown) or includes (not shown) a controller 135. The controller 135 may have a processing circuitry and a memory (not shown) including instructions for running olfactory training exercises, for example, based on training exercise data received from the scent orchestrator 120.

Each of the user device 140 and the MPD 150 may be, but is not limited to, a personal computer, a laptop, a tablet computer, a smartphone, a wearable computing device, any device capable of receiving and displaying notifications, a combination thereof, and the like. In some embodiments, the user device 140 has installed thereon a software application (not shown) or other software utilized for olfactory training as described herein. As a non-limiting example, such software may cause display of options to be presented to the user during each olfactory training exercise, and may further be adapted to accept user inputs indicating answers to questions presented during olfactory training exercises (e.g., a selection of one of the scent options displayed to the user which the user makes based on the scent they smelled dispensed by the SDD 130).

The MPD 150 is configured with one or more input devices (not shown) for receiving user inputs, for example, from a medical professional. User inputs may include, but are not limited to, selections of scents to be dispensed during training exercises, selections of options to be presented during training exercises (i.e., cards), both, and the like. The user inputs received via the MPD 150 may be sent to, for example, the scent orchestrator 120 for use in generating olfactory training exercise data as described herein.

A hardware layer of computing components which may be utilized to realize any or all of the scent orchestrator 120, the SDD 130, the user device 140, or the MPD 150, is described further below with respect to FIG. 9.

It should be noted that the scent orchestrator 120, the controller 135, the user device 140, and the MPD 150 are depicted as separate components communicating over the network 110 for simplicity but that, at least in some embodiments, the components are not limited to such a deployment. In some embodiments, a single system may be configured to perform the activities of more than one of the scent orchestrator 120, the SDD 130, the user device 140, and the MPD 150. Additionally, in some implementations, the SDD 130 may communicate with the user device directly, for example, via Bluetooth or other local connections.

Figure 2:
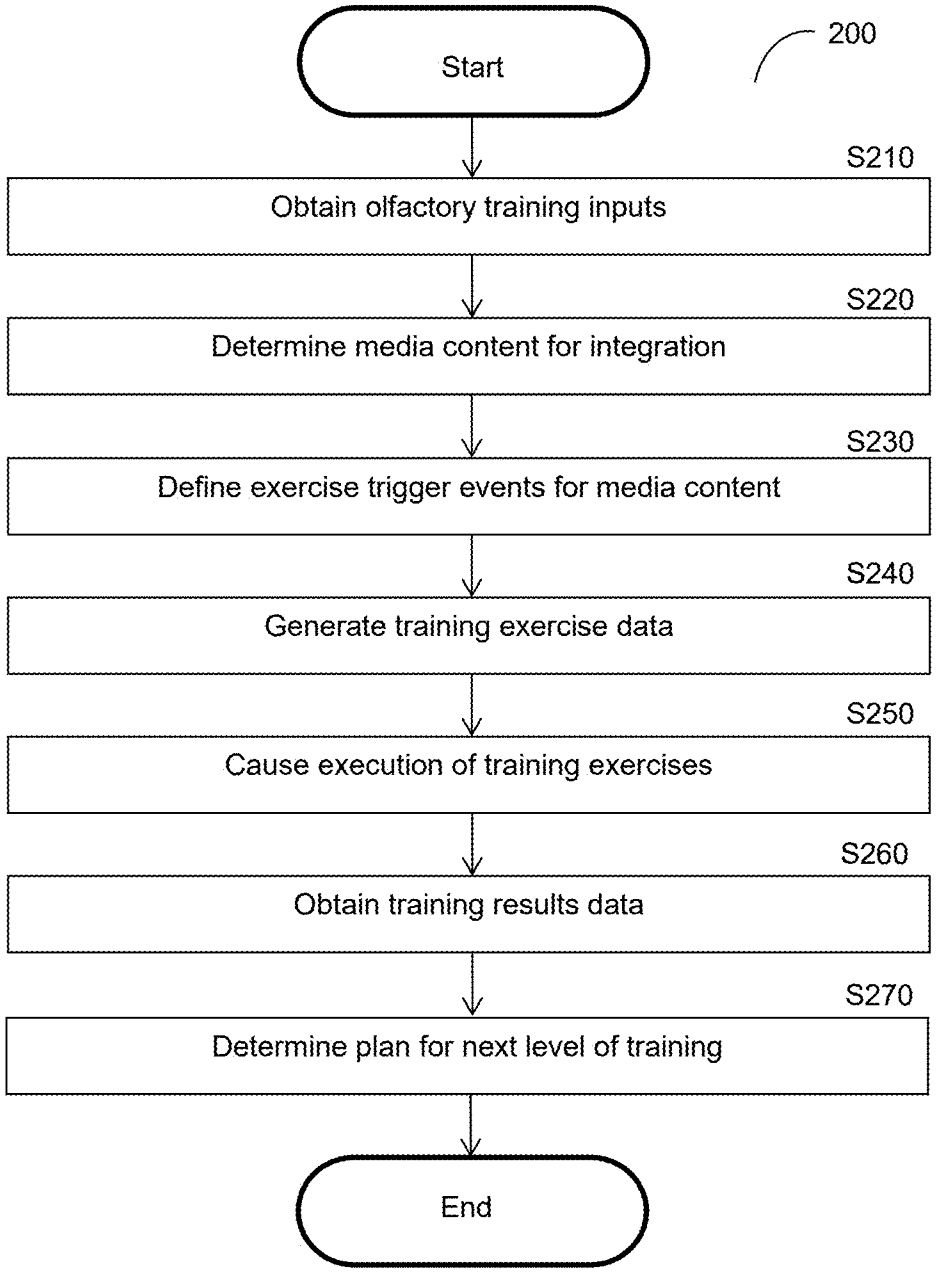
FIG. 2 is a flowchart illustrating a method for olfactory training using a scent dispensing device according to an embodiment.

FIG. 2 is a flowchart 200 illustrating a method for olfactory training using a scent dispensing device according to an embodiment. In an embodiment, the method is performed by the scent orchestrator 120 or the SDD 130, FIG. 1.

At S210, one or more inputs for olfactory training are obtained. The obtained olfactory training inputs may be, for example, scents to be dispensed, options to be presented, media content or a location of media content, trigger event definitions, sequences or other orders of training exercises, a combination thereof, and the like. The inputs may be obtained from one or more other devices or systems such as, but not limited to, the user device 140, the MPD 150, and the like. The inputs therefore define exercises as well as parameters related to operation of the exercises.

At optional S220, media content for integration with the olfactory training is determined. The media content may include, but is not limited to, video (e.g., a movie), a video game, images, audio content, a combination thereof, and the like. The media content determined at S220 may be included among the inputs obtained at S210, may be identified via the inputs obtained at S210 (as indicated by an address or other location of the media content), and the like. In accordance with various disclosed embodiments, the olfactory training exercises may be operated in coordination with the media content, for example during pauses in the media content or while the media content is being provided to the user. That is, the olfactory training exercises may be operated such that a scent dispensing device dispenses scents at times defined with respect to the media content (e.g., times corresponding to the occurrence of trigger events defined with respect to the media content).

At optional S230, exercise trigger events are defined. In an embodiment, the exercise trigger events are defined such that scents are dispensed when the trigger events occur. A non-limiting example of a trigger event includes specific timestamps in a movie where a correlating scent can be dispensed (i.e., a coffee scent dispensed at 5:00 in a movie where a character is shown drinking coffee at 5:00). In some embodiments, trigger events may be defined based on actions of the user such as, but not limited to, choices made by a user in a video game. In such an embodiment, when a certain action which is a trigger event is performed, a scent may be dispensed according to a corresponding training exercise for that trigger event.

At S240, training exercise data is generated based on the obtained inputs. In an embodiment, the training exercise data includes instructions for dispensing scents in accordance with one or more training exercises determined based on the user inputs. In a further embodiment, the training exercise data may further include data to be displayed as part of the training exercises (e.g., options to be presented for a user to select from based on scents they smelled during the training exercises).

In some implementations, the training exercise data may be organized in an order, for example, an order indicated among the inputs obtained at S210. In this regard, the training exercises may be operated according to the order. Alternatively, training exercises may be defined based on trigger events as described above such that the training exercise data includes one or more trigger events for each training exercise, and each training exercise is operated when its respective trigger events have occurred.

In some embodiments, the training exercise data includes scents to be dispensed according to training exercises involving options presented via physical items such as, but not limited to, cards depicting potential options.

At S250, the olfactory training exercises are caused to be operated based on the training exercise data.

In an embodiment, S250 includes sending the training exercise data to the SDD 130, the user device 140, both, or the like. The training exercise data is sent such that the olfactory training exercises can be operated using the training exercise data in the presence of a user acting as a trainee undergoing training according to the olfactory training exercises. Alternatively, S250 may include operating the olfactory training exercises via dispensing of scents, displaying of options, or both.

At S260, training results data is obtained based on user inputs received during or otherwise in response to the training exercises. To this end, the training results data may include, but is not limited to, selections made by the user (e.g., a selection of a scent the user believes they smelled during each training exercise).

At S270, a plan for the next level of training is determined. In an embodiment, the plan is determined based on the training results data. In some embodiments, the plan is determined based further on one or more other factors, such as but not limited to, user data (i.e., age, medical condition, goal, etc.), doctor recommendations, scent availability (i.e., remaining scents in the SDD 130), a combination thereof, and the like.

In some embodiments, the plan includes a difficulty for the next level of training. As a non-limiting example, a harder level of training could be utilized during the next level of training if, for example, the user performed well during the last set of training exercises (e.g., as indicated by a score determined based on the number or proportion of accurate selections of scents made by the user which match the scent dispensed during each olfactory training exercise).

In some embodiments, the plan for the next level of training may be determined based on the user's success in relation to different scent categories. As a non-limiting example, if the user's score as to citrus scents (e.g., lime, lemon, orange, etc.) is poor, then a plan can be determined to include more citrus scents. As another non-limiting example, if the user's score as to earthy scents (e.g., pine, moss, grass, etc.) is high, then a plan can be determined to include fewer earthy scents.

Figure 3:
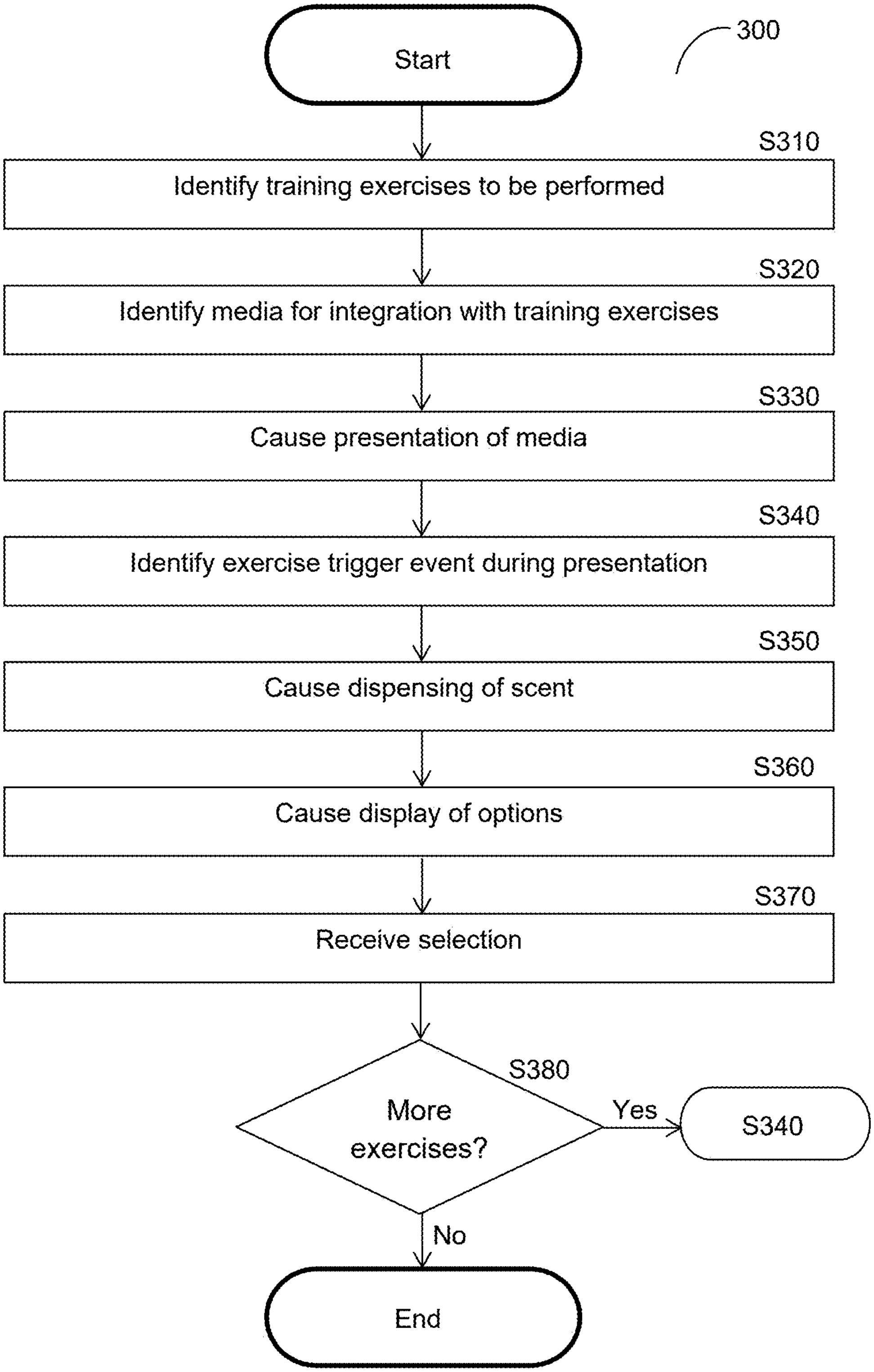
FIG. 3 is a flowchart illustrating a method for conducting olfactory training exercises according to an embodiment.

FIG. 3 is a flowchart 300 illustrating a method for conducting olfactory training exercises according to an embodiment. In an embodiment, the method is performed by the SDD 130, the controller 135, the user device 140, a combination thereof, and the like, FIG. 1.

At S310, olfactory training exercises to be performed are identified. The training exercises may be identified in training exercise data, for example training exercise data generated as described above with respect to FIG. 2. In an embodiment, the olfactory training exercises at least include dispensing of respective scents, and may further include displaying options or integrating with media content as described herein.

At optional S320, media content for integration with training exercises is identified. The media content may be media content included or indicated in training exercise data. In some embodiments, the identified media content may be projected or otherwise presented to the user during olfactory training exercises, between olfactory training exercises, and the like.

At optional S330, the media content is caused to be presented. As a non-limiting example, a movie may be caused to be played via a user device of a user which is communicatively connected to a scent dispensing device being used to dispense scents during the olfactory training exercises.

At optional S340, one or more trigger events are identified. The identified trigger events may be defined in the training exercise data, and may correspond to an olfactory training exercise among olfactory training exercises represented in the training exercise data. As noted above, in some embodiments, olfactory training exercises are operated when their respective trigger events have occurred.

At S350, the dispensing of the scent is caused, thereby operating one of the training exercises. To this end, S350 may include dispensing the scent (e.g., via a scent dispensing device such as the SDD 130, FIG. 1) or sending a command to dispense a scent (e.g., via a user device such as the user device 140, FIG. 1).

At optional S360, one or more options may be displayed. As a non-limiting example, options of potential answers to a question (e.g., "Which scent do you smell now?") may be displayed via a display on a scent dispensing device or a user device communicatively connected to the scent dispensing device. Alternatively, the options may be presented to the user without displaying the options, for example using a guided exercise manual and playing cards indicating the options.

At S370, one or more user inputs indicating a selection of one of the options is received. As a non-limiting example, one of the options may be "Banana" indicating that the user believes the scent they smelled is that of a banana. In some embodiments in which physical items such as cards are used to present options, the user observing the physical items may select a scent and provide user inputs, for example, via their smartphone or other user device (e.g., the user device 140, FIG. 1).

At S380, it is determined if additional training exercises are to be performed and, if so, execution continues S340, otherwise, execution terminates. In some implementations, training exercises may be performed until all training exercises in a set have been performed or until all potential trigger conditions have been exhausted. In other implementations, additional training exercises may be performed until any integrated media content is completed or otherwise turned off.

Figure 4:
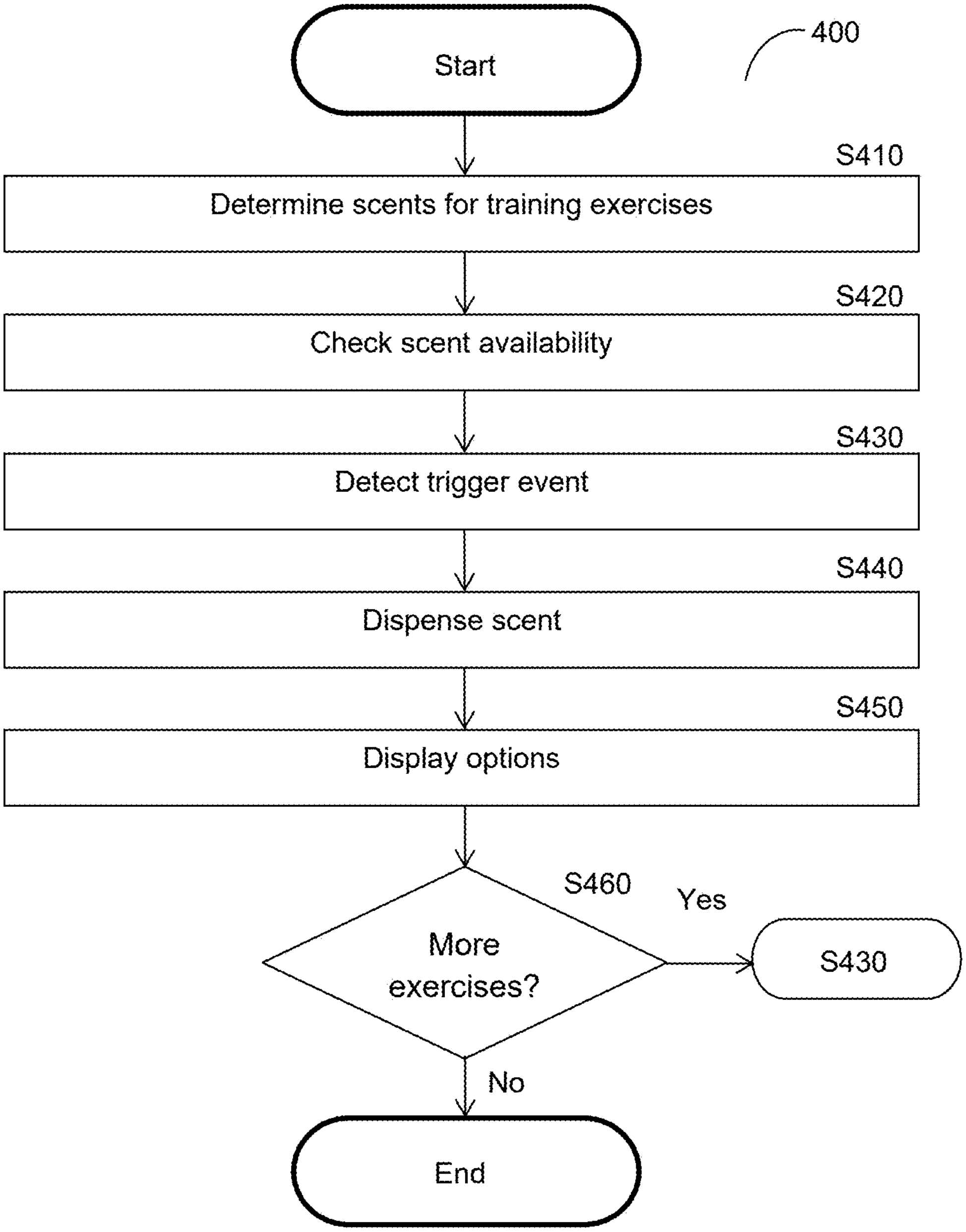
FIG. 4 is a flowchart illustrating a method for dispensing scents during olfactory training exercises according to an embodiment.

FIG. 4 is a flowchart 400 illustrating a method for dispensing scents during olfactory training exercises according to an embodiment. In an embodiment, the method is performed by the SDD 130, FIG. 1.

At S410, scents for olfactory training exercises are determined. In an embodiment, the scents are determined based on instructions, for example, instructions received from a scent orchestrator (e.g., the scent orchestrator 120, FIG. 1).

At optional S420, scent availability is checked. In an embodiment, S420 includes checking an amount of scent essence in chambers of a scent dispensing device which will be utilized to perform the olfactory training exercises. More specifically, amounts of scent essences required to dispense each scent required by the olfactory training exercises may be determined in order to confirm that sufficient amounts of each scent essence are available. In some implementations, if any scents are not available (i.e., if an amount of one or more scent essences required to dispense the scent are not available), a notification may be generated and sent indicating the lack of availability in order to prompt refilling of chambers of the scent dispensing device.

At optional S430, a trigger event is detected. As noted above, the trigger event may be based on passage of time, completion of other olfactory training exercises, certain interactions with media content, a combination thereof, a portion thereof, and the like.

At S440, a scent is dispensed according to one of the olfactory training exercises. In an embodiment, dispensing the scent includes dispensing one or more scent essences from respective chambers of a scent dispensing device. As a non-limiting example, a candy cane scent can be dispensed by dispensing a peppermint scent essence and a strawberry scent essence. When trigger events are utilized, the scent is dispensed for an olfactory training exercise corresponding to one or more trigger events that have occurred when the trigger events have occurred.

At optional S450, options are displayed via a display such as, but not limited to, a display of the scent dispensing device. Alternatively, the options may be displayed via a display of another device (e.g., the user device 140, FIG. 1), or the options may not be displayed (e.g., when the options are presented via physical items such as cards).

At S460, it is determined if additional training exercises are to be performed and if so, execution continues with S430, otherwise execution terminates.

Figure 5:
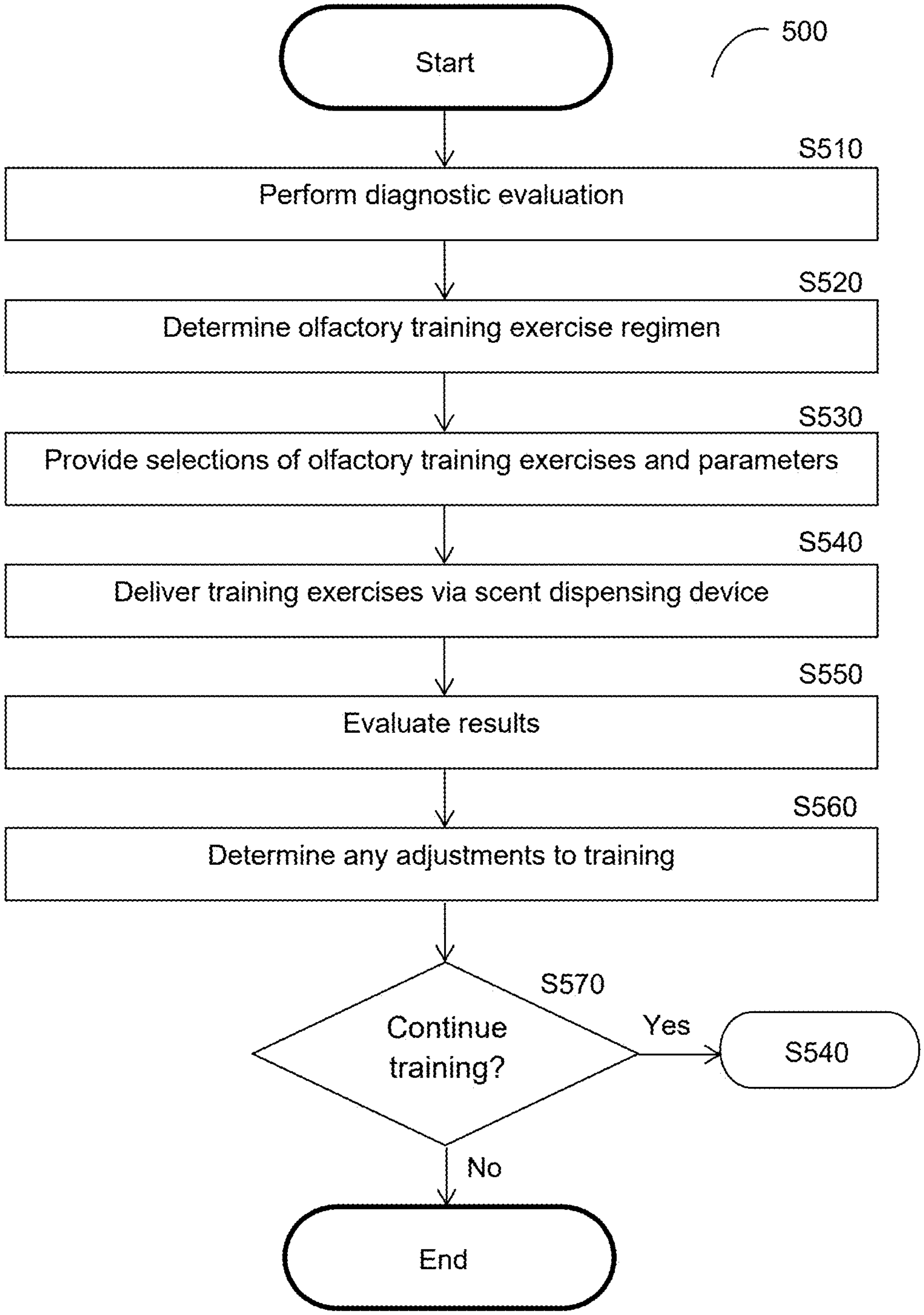
FIG. 5 is a flowchart illustrating a method for treating anosmia using a scent dispensing device according to an embodiment.
Figure 6A:
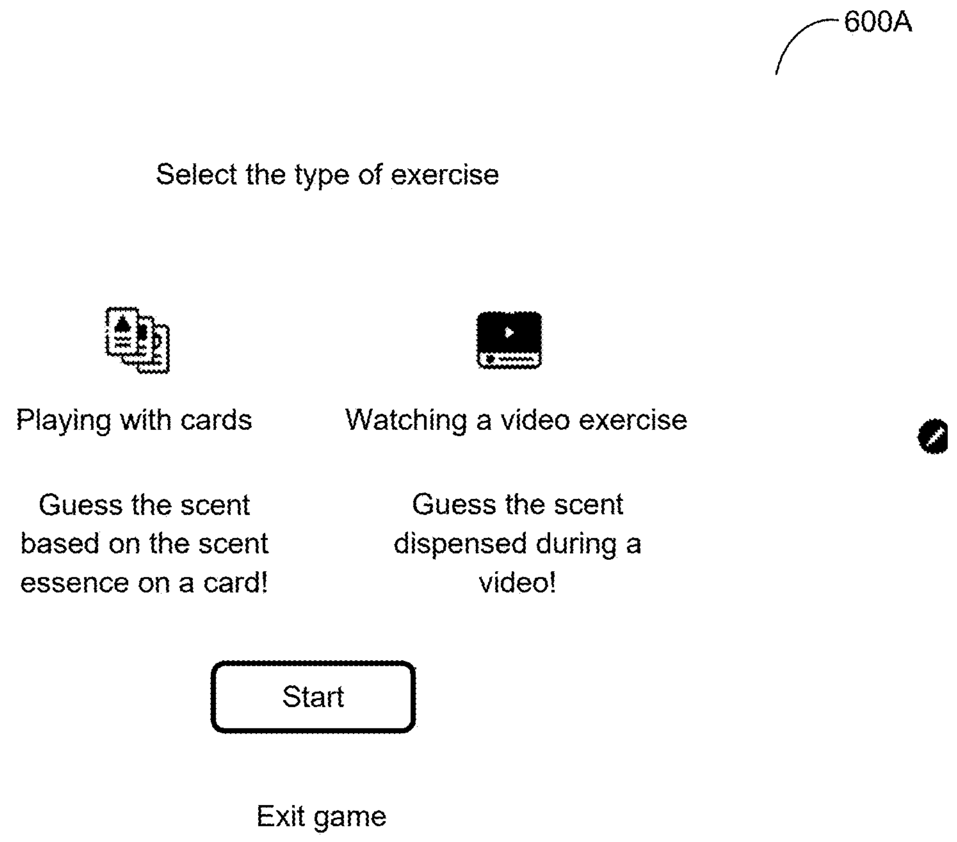
FIGS. 6A-E are example screenshots of user interfaces which may be displayed in accordance with various disclosed embodiments.
Figure 6B:
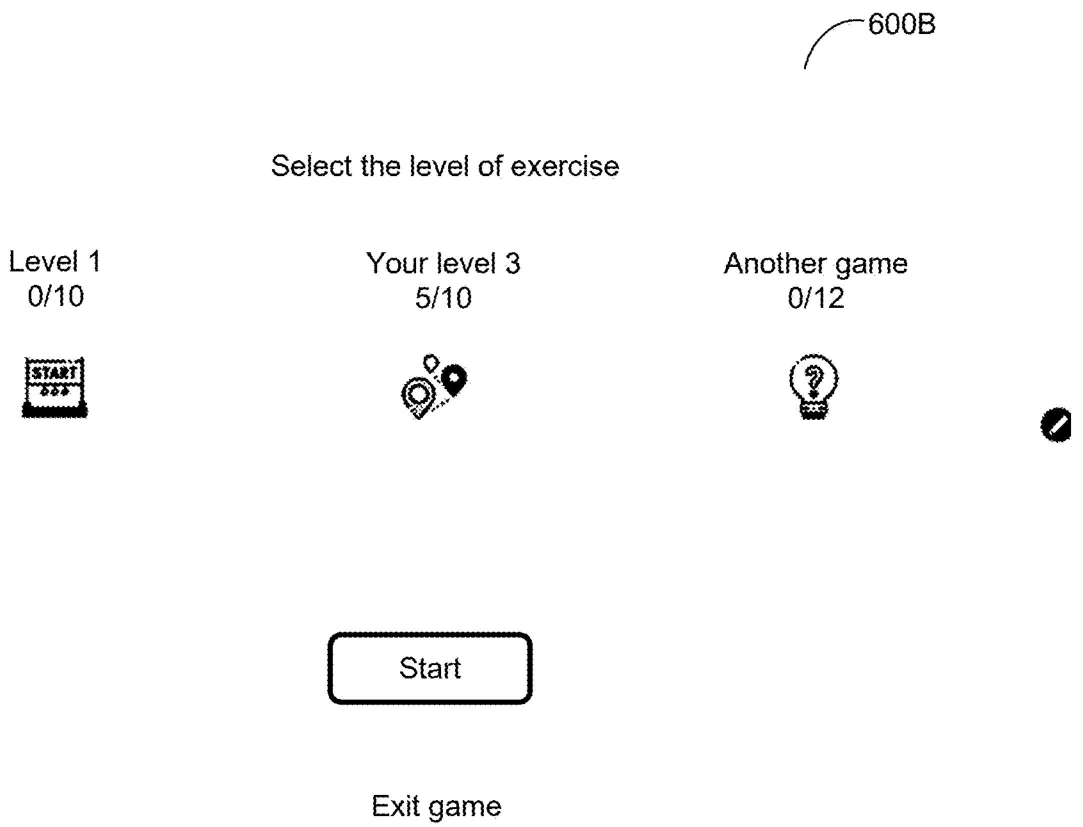
Figure 6C:
Figure 6D:
Figure 6E:
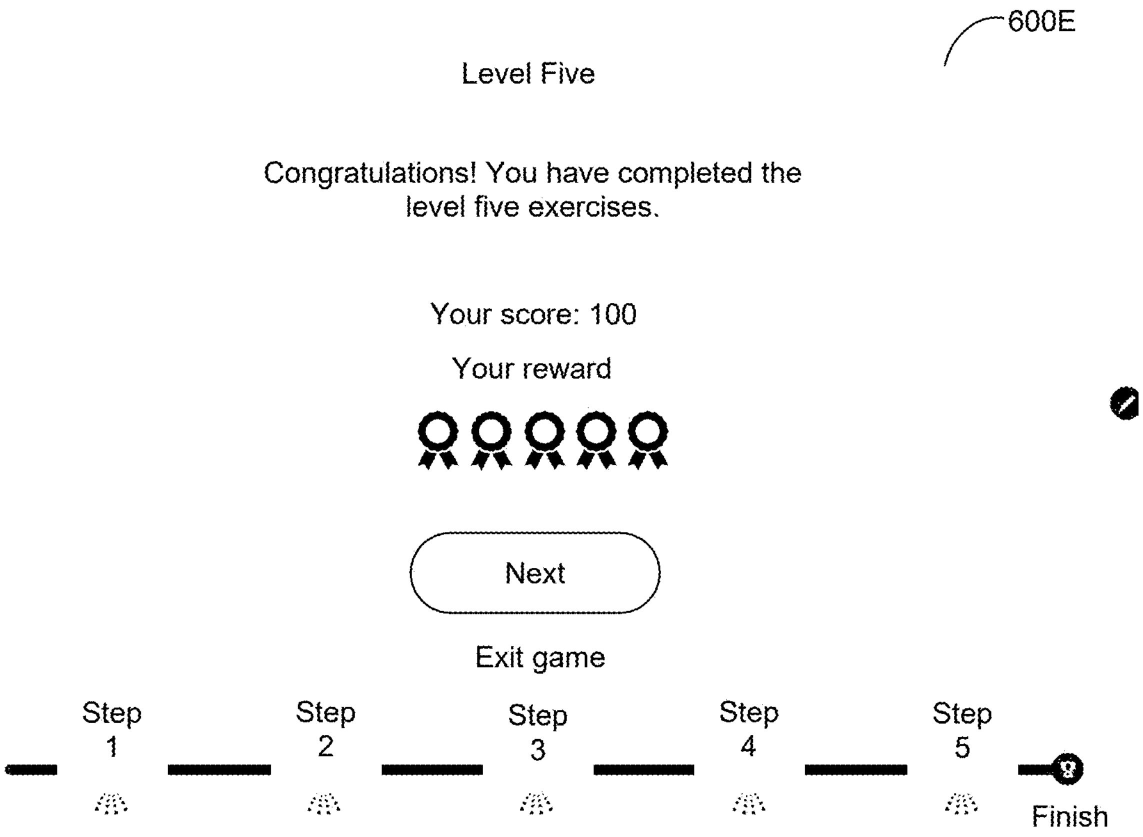

FIG. 5 is a flowchart 500 illustrating a method for treating loss of smell such as anosmia or hyposmia using a scent dispensing device according to an embodiment.

At S510, a diagnostic evaluation is performed with respect to a patient. The diagnostic evaluation may be performed, for example, in order to determine a degree of smell loss, particular scents which are not recognized by the patient, both, and the like.

At S520, an olfactory training exercise regimen is determined. The olfactory training exercise regimen includes one or more olfactory training exercises to be performed in order to rehabilitate the patient's sense of smell.

At S530, selections of scents and parameters for olfactory training exercises are provided. The parameters for the exercises may include, but are not limited to, trigger events, media for integration with olfactory training exercises, orders of scents to be dispensed, options to present to the patient during each training exercise, combinations thereof, and the like.

At S540, olfactory training exercises are delivered via a scent dispensing device (e.g., the SDD 130, FIG. 1). In an embodiment, the scent dispensing device includes multiple chambers, each chamber adapted to receive and dispense a respective scent essence. The training exercises are delivered via dispensing of one or more scent essences from the scent dispensing device in order to dispense respective scents for each of the olfactory training exercises.

At S550, results of the olfactory training exercises are evaluated. Evaluating the results may include, but is not limited to, determining a number or proportion of correct answers (e.g., answers indicated by options selected by the patient during the olfactory training exercises, where correct answers are answers indicating the scent which was dispensed in a given olfactory training exercise), determining a score for the patient's performance, and the like. Evaluating the results may further include further diagnosing the patient, for example, diagnosing a new degree for the patient's sense of smell.

At S560, any adjustments to training are determined based on the evaluation of the results. As a non-limiting example, if the patient scored well (e.g., above a threshold value), the training may be adjusted to increase difficulty (e.g., such that the next set of training exercises may include scents that are closer in smell and therefore harder to distinguish from each other).

At S570, it is determined if more training exercises are to be performed and, if so, execution continues with S540, otherwise, execution terminates. In some implementations, the determination at S570 may be based on the evaluation of the performance results.

FIGS. 6A-E are example screenshots 600A through 600E, respectively, of user interfaces which may be displayed in accordance with various disclosed embodiments.

The example screenshot 600A illustrates potential types of olfactory training exercises from which the user may select. In the non-limiting example shown in FIG. 6A the types of exercises shown include playing with cards (e.g., physical playing cards) or watching a video exercise (i.e., integrated media content).

The example screenshot 600B illustrates levels for olfactory training exercises from which the user may select. For example, the user may select from among a beginner level (e.g., level 1), their current level (e.g., as determined based on previous olfactory training results), a predetermined game configuration, and the like.

The example screenshot 600C illustrates a non-limiting example of different options presented to a user representing respective scents which the user might smell during a given olfactory training exercise. In the non-limiting example screenshot 600C, the options include an option corresponding to banana scent and an option corresponding to chocolate scent. The example screenshot 600D illustrates a user selection of the banana scent option.

The example screenshot 600E illustrates a score determined based on results of the olfactory training exercises. In the non-limiting example shown in FIG. 6E, the user guessed all scents correctly and therefore received a score of 100.

Figure 7:
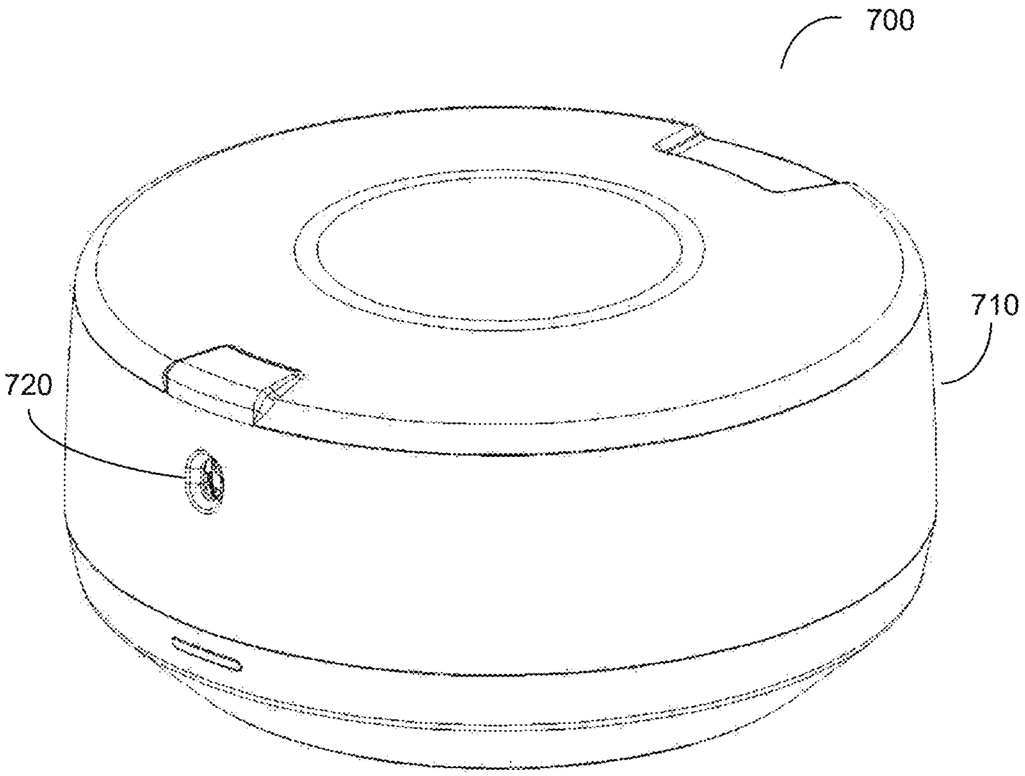
FIG. 7 is an illustration of a scent dispensing device which may be utilized in accordance with various disclosed embodiments.

FIG. 7 is an illustration of a scent dispensing device 700 which may be utilized in accordance with various disclosed embodiments. The scent dispensing device 700 depicted in FIG. 7 includes a housing 710 and an aperture 720. Scents dispensed as part of training in accordance with various disclosed embodiments may be produced via components disposed in the housing 710 and ejected through the aperture 720, thereby dispensing the produced scent in an area surrounding the scent dispensing device 700. In some implementations, the aperture 720 may be an opening of a nozzle (not shown), which may be a pipe or tube adapted to direct an external flow of a scent disposed within the housing 710.

In some implementations, the scent dispensing device 700 includes a multi-chamber drum having a body including multiple chambers, where each chamber is adapted to receive a respective scent essence. A non-limiting example of such an implementation which may be utilized in accordance with various disclosed embodiments is shown in FIG. 8, which shows a multi-chamber drum 800 which may be utilized as part of a scent dispensing device in accordance with the various disclosed embodiments.

In an embodiment, the scent dispenser includes a drum having a body. The body includes: a plurality of chambers; a plurality of actuators, respective of the chambers; a first motor; a second motor; and a local control unit. The chambers are disposed along a base on the interior of the body, each of the chambers configured to receive a respective scent essence. Each of the actuators includes an actuator port, configured to be aligned in a selected direction in relation to the body. The first motor is configured to drive the application of pressure in a selected actuator so as to induce emission of a scent essence through the actuator port. The second motor is configured to drive the displacement of at least a portion of the body. The local control unit, responsive of scent emission instructions, is configured to selectively activate the second motor to displace the body, so as to align with the nozzle a selected actuator port of an actuator respective of the selected chamber, and configured to selectively activate the first motor to induce emission of the scent essence contained in the selected chamber through the selected actuator port, so as to produce a scent emission directed to the external environment through the nozzle. The scent producer may further include a plurality of valves, each of the valves configured to dispense a scent essence into a respective one of the chambers. The scent producer may further include a cam, coupled to the first motor; a push member; a rocker; and a piston, where the first motor is driven so as to rotate the cam to drive the piston via the push member and the rocker, so as to depress the selected actuator to force at least a portion of the scent essence in the respective chamber to exit via the selected actuator port. The chambers may be disposed radially about a longitudinal axis of the body. The scent producer may further include a plurality of receptacles, each one of the receptacles associated with a respective chamber and to receive a respective actuator, where each of the actuators comprises a respective fin, and each of the receptacles comprises a respective slot, the respective fin configured to engage within a respective slot so as to maintain a direction of the respective actuator port. The housing may include a cover, and a shell, whereby the cover is configured to engage securely with the shell so as to encase the body, and where the nozzle extends through a wall of the cover, providing a pathway thereto from the selected actuator port to the external environment. The scent producer may further include a tray, where the body is secured to the tray and configured to rotate within the shell of the housing, in response to activation of the second motor. The chambers may be separated by a respective radial wall extending from an inner band to an inner wall of the base, each of the inner band and the inner wall describing a substantially circular band at a predetermined radial distance from a longitudinal axis of the body, the radial distance of the inner wall being greater than the radial distance of the inner band. The body may be a circular body, where the second motor is a rotation motor configured to rotate the chambers, so as to align the selected actuator port of the selected actuator respective of the selected chamber, with the nozzle. The body may be a linear body, where the second motor is configured to translate the chambers, so as to align the selected actuator port of the selected actuator respective of the selected chamber, with the nozzle.

Figure 8:
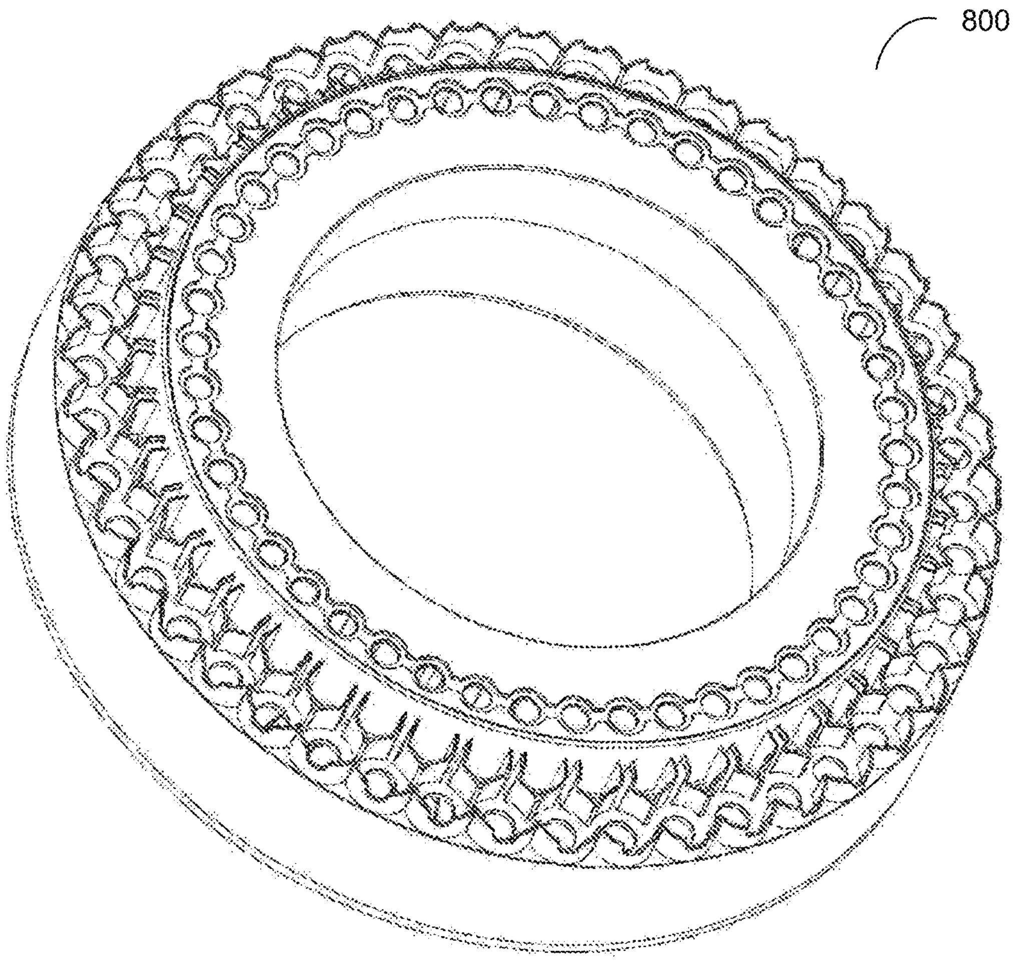
FIG. 8 is an illustration of a multi-chamber drum which may be utilized as part of a scent dispensing device in accordance with various disclosed embodiments.

The multi-chamber drum 800 depicted in FIG. 8 may further include actuators (not shown), which each actuator having an actuator port adapted to be aligned in a selected direction in relation to the body. The scent dispensing device may further include motors (not shown) such as a first motor configured to drive application of pressure in one of the actuators so as to induce emission of a scent essence through the respective actuator port. The second motor is configured to drive displacement of at least a portion of the body.

A non-limiting example design of a scent dispensing device which may be utilized in accordance with at least some of the disclosed embodiments is discussed in the above-referenced International Patent Application No. PCT/IL2022/051351, assigned to the common assignee, the contents of which are hereby incorporated by reference.

Figure 9:
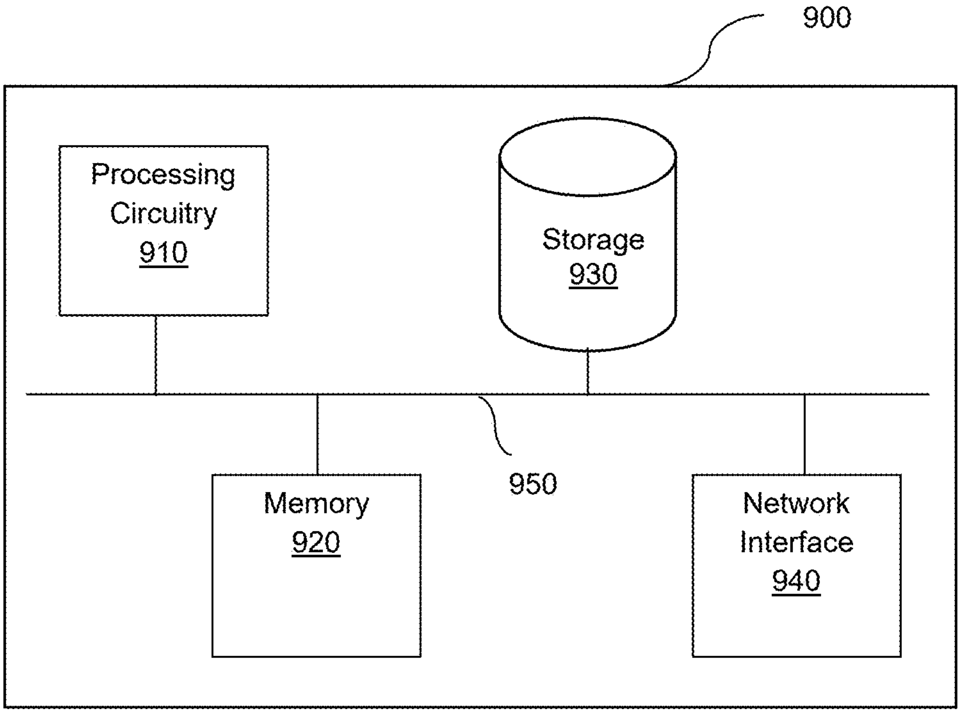
FIG. 9 is a schematic diagram of a scent orchestrator according to an embodiment.

FIG. 9 is an example schematic diagram of hardware layer 900 which may be utilized according to various disclosed embodiments. The hardware layer 900 or a similarly configured hardware layer may be utilized to realize one or more of the disclosed embodiments, for example, in use as part of the scent orchestrator 120, the controller 135, the user device 140, or the MPD 150, FIG. 1.

The hardware layer 900 includes a processing circuitry 910 coupled to a memory 920, a storage 930, and a network interface 940. In an embodiment, the components of the hardware layer 900 may be communicatively connected via a bus 950.

The processing circuitry 910 may be realized as one or more hardware logic components and circuits. For example, and without limitation, illustrative types of hardware logic components that can be used include field programmable gate arrays (FPGAs), application-specific integrated circuits (ASICs), Application-specific standard products (ASSPs), system-on-a-chip systems (SOCs), graphics processing units (GPUs), tensor processing units (TPUs), general-purpose microprocessors, microcontrollers, digital signal processors (DSPs), and the like, or any other hardware logic components that can perform calculations or other manipulations of information.

The memory 920 may be volatile (e.g., random access memory, etc.), non-volatile (e.g., read only memory, flash memory, etc.), or a combination thereof.

In one configuration, software for implementing one or more embodiments disclosed herein may be stored in the storage 930. In another configuration, the memory 920 is configured to store such software. Software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the processing circuitry 910, cause the processing circuitry 910 to perform the various processes described herein.

The storage 930 may be magnetic storage, optical storage, and the like, and may be realized, for example, as flash memory or other memory technology, compact disk-read only memory (CD-ROM), Digital Versatile Disks (DVDs), or any other medium which can be used to store the desired information.

The network interface 940 allows the hardware layer to communicate with, for example, the scent orchestrator 120, the SDD 130, the user device 140, the MPD 150, or a combination thereof.

It should be understood that the embodiments described herein are not limited to the specific architecture illustrated in FIG. 9, and other architectures may be equally used without departing from the scope of the disclosed embodiments.

It is important to note that the embodiments disclosed herein are only examples of the many advantageous uses of the innovative teachings herein. In general, statements made in the specification of the present application do not necessarily limit any of the various claimed embodiments. Moreover, some statements may apply to some inventive features but not to others. In general, unless otherwise indicated, singular elements may be in plural and vice versa with no loss of generality. In the drawings, like numerals refer to like parts through several views.

The various embodiments disclosed herein can be implemented as hardware, firmware, software, or any combination thereof. Moreover, the software is preferably implemented as an application program tangibly embodied on a program storage unit or computer readable medium consisting of parts, or of certain devices and/or a combination of devices. The application program may be uploaded to, and executed by, a machine comprising any suitable architecture. Preferably, the machine is implemented on a computer platform having hardware such as one or more central processing units ("CPUs"), a memory, and input/output interfaces. The computer platform may also include an operating system and microinstruction code. The various processes and functions described herein may be either part of the microinstruction code or part of the application program, or any combination thereof, which may be executed by a CPU, whether or not such a computer or processor is explicitly shown. In addition, various other peripheral units may be connected to the computer platform such as an additional data storage unit and a printing unit. Furthermore, a non-transitory computer readable medium is any computer readable medium except for a transitory propagating signal.

All examples and conditional language recited herein are intended for pedagogical purposes to aid the reader in understanding the principles of the disclosed embodiment and the concepts contributed by the inventor to furthering the art, and are to be construed as being without limitation to such specifically recited examples and conditions. Moreover, all statements herein reciting principles, aspects, and embodiments of the disclosed embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

It should be understood that any reference to an element herein using a designation such as "first," "second," and so forth does not generally limit the quantity or order of those elements. Rather, these designations are generally used herein as a convenient method of distinguishing between two or more elements or instances of an element. Thus, a reference to first and second elements does not mean that only two elements may be employed there or that the first element must precede the second element in some manner. Also, unless stated otherwise, a set of elements comprises one or more elements.

As used herein, the phrase "at least one of" followed by a listing of items means that any of the listed items can be utilized individually, or any combination of two or more of the listed items can be utilized. For example, if a system is described as including "at least one of A, B, and C," the system can include A alone; B alone; C alone; 2A; 2B; 2C; 3A; A and B in combination; B and C in combination; A and C in combination; A, B, and C in combination; 2A and C in combination; A, 3B, and 2C in combination; and the like.

What is claimed is:

1. A method for olfactory training, comprising:

defining a plurality of exercise trigger events based on inputs indicating a plurality of first scents to be dispensed during a plurality of first olfactory training exercises, wherein each exercise trigger event of the plurality of exercise trigger events corresponds to a respective scent of the plurality of first scents;

generating olfactory training exercise data based on the inputs indicating the plurality of first scents to be dispensed during the plurality of first olfactory training exercises; and causing a scent dispensing device to dispense the plurality of first scents based on the olfactory training exercise data, each scent of the plurality of first scents being dispensed during operation of a respective first olfactory training exercise of the plurality of first olfactory training exercises, wherein the scent dispensing device includes a plurality of chambers, wherein each chamber of the plurality of chambers includes a respective scent essence of a plurality of scent essences, wherein dispensing each scent of the plurality of first scents includes causing at least one scent essence of the plurality of scent essences to be dispensed via at least a portion of the plurality of chambers of the scent dispensing device, wherein the plurality of first scents is dispensed such that the respective scent of the plurality of first scents is dispensed at a time defined with respect to the corresponding exercise trigger event of the plurality of exercise trigger events;

determining at least one training adjustment based on a performance of a user with respect to at least one scent category during the plurality of first olfactory training exercises, wherein the at least one training adjustment includes an adjustment to a number of different scents belonging to the at least one scent category to be dispensed during at least one second olfactory training exercise; and adjusting training by performing the at least one second olfactory training exercise, wherein the at least one second olfactory training exercise is generated based on the plurality of first olfactory training exercises and the at least one training adjustment, wherein performing the at least one second olfactory training exercise includes dispensing at least one second scent via the scent dispensing device.

2. The method of claim 1, wherein the olfactory training exercise data further includes an order for the plurality of first olfactory training exercises, wherein the plurality of first scents is dispensed according to the order.

3. The method of claim 1, wherein the scent dispensing device is caused to dispense the plurality of first scents while media content is playing, wherein each scent of the plurality of first scents is dispensed at a time corresponding to the respective exercise trigger event of the plurality of exercise trigger events defined with respect to the media content.

4. The method of claim 1, wherein the scent dispensing device further includes a plurality of actuators adapted to manipulate the plurality of scent essences disposed in the plurality of chambers, wherein causing the scent dispensing device to dispense the plurality of first scents further includes causing the scent dispensing device to drive application of pressure in at least one actuator of the plurality of actuators in order to induce emission of the at least one scent essence of the plurality of scent essences.

5. The method of claim 1, wherein the plurality of chambers is disposed in a drum, wherein the scent dispensing device has a housing with an aperture, wherein causing the scent dispensing device to dispense the plurality of first scents further includes causing the scent dispensing device to rotate the drum in order to align at least one chamber of the plurality of chambers with the aperture.

6. The method of claim 1, wherein a score of the performance of the user with respect to a first scent category of the at least one scent category is above a threshold, wherein the at least one training adjustment includes increasing a number of scents belonging to the first scent category.

7. The method of claim 6, wherein the plurality of first olfactory training exercises includes dispensing scents from a first number of chambers among the plurality of chambers corresponding to the first scent category, wherein the at least one training adjustment includes dispensing scents from a second number of chambers among the plurality of chambers corresponding to the first scent category, wherein the second number of chambers is higher than the first number of chambers.

8. A non-transitory computer-readable medium having stored thereon instructions for causing a processing circuitry to execute a process, the process comprising:

defining a plurality of exercise trigger events based on inputs indicating a plurality of first scents to be dispensed during a plurality of first olfactory training exercises, wherein each exercise trigger event of the plurality of exercise trigger events corresponds to a respective scent of the plurality of first scents;

generating olfactory training exercise data based on the inputs indicating the plurality of first scents to be dispensed during the plurality of first olfactory training exercises; and causing a scent dispensing device to dispense the plurality of first scents based on the olfactory training exercise data, each scent of the plurality of first scents being dispensed during operation of a respective first olfactory training exercise of the plurality of first olfactory training exercises, wherein the scent dispensing device includes a plurality of chambers, wherein each chamber of the plurality of chambers includes a respective scent essence of a plurality of scent essences, wherein dispensing each scent of the plurality of first scents includes causing at least one scent essence of the plurality of scent essences to be dispensed via at least a portion of the plurality of chambers of the scent dispensing device, wherein the plurality of first scents is dispensed such that the respective scent of the plurality of first scents is dispensed at a time defined with respect to the corresponding exercise trigger event of the plurality of exercise trigger events;

determining at least one training adjustment based on a performance of a user with respect to at least one scent category during the plurality of first olfactory training exercises, wherein the at least one training adjustment includes an adjustment to a number of different scents belonging to the at least one scent category to be dispensed during at least one second olfactory training exercise; and adjusting training by performing the at least one second olfactory training exercise, wherein the at least one second olfactory training exercise is generated based on the plurality of first olfactory training exercises and the at least one training adjustment, wherein performing the at least one second olfactory training exercise includes dispensing at least one second scent via the scent dispensing device.

9. A system for olfactory training, comprising:

a processing circuitry; and a memory, the memory containing instructions that, when executed by the processing circuitry, configure the system to:

define a plurality of exercise trigger events based on inputs indicating a plurality of first scents to be dispensed during a plurality of first olfactory training exercises, wherein each exercise trigger event of the plurality of exercise trigger events corresponds to a respective scent of the plurality of first scents;

generate olfactory training exercise data based on the inputs indicating the plurality of first scents to be dispensed during the plurality of first olfactory training exercises; and cause a scent dispensing device to dispense the plurality of first scents based on the olfactory training exercise data, each scent of the plurality of first scents being dispensed during operation of a respective first olfactory training exercise of the plurality of first olfactory training exercises, wherein the scent dispensing device includes a plurality of chambers, wherein each chamber of the plurality of chambers includes a respective scent essence of a plurality of scent essences, wherein dispensing each scent of the plurality of first scents includes causing at least one scent essence of the plurality of scent essences to be dispensed via at least a portion of the plurality of chambers of the scent dispensing device, wherein the plurality of first scents is dispensed such that the respective scent of the plurality of first scents is dispensed at a time defined with respect to the corresponding exercise trigger event of the plurality of exercise trigger events;

determine at least one training adjustment based on a performance of a user with respect to at least one scent category during the plurality of first olfactory training exercises, wherein the at least one training adjustment includes an adjustment to a number of different scents belonging to the at least one scent category to be dispensed during at least one second olfactory training exercise; and adjust training by performing the at least one second olfactory training exercise, wherein the at least one second olfactory training exercise is generated based on the plurality of first olfactory training exercises and the at least one training adjustment, wherein performing the at least one second olfactory training exercise includes dispensing at least one second scent via the scent dispensing device.

10. The system of claim 9, wherein the olfactory training exercise data further includes an order for the plurality of first olfactory training exercises, wherein the plurality of first scents is dispensed according to the order.

11. The system of claim 9, wherein the scent dispensing device is caused to dispense the plurality of first scents while media content is playing, wherein each scent of the plurality of first scents is dispensed at a time corresponding to a respective exercise trigger event of the plurality of exercise trigger events defined with respect to the media content.

12. The system of claim 9, wherein the scent dispensing device further includes a plurality of actuators adapted to manipulate the plurality of scent essences disposed in the plurality of chambers, wherein causing the scent dispensing device to dispense the plurality of first scents further includes causing the scent dispensing device to drive application of pressure in at least one actuator of the plurality of actuators in order to induce emission of the at least one scent essence of the plurality of scent essences.

13. The system of claim 9, wherein the plurality of chambers is disposed in a drum, wherein the scent dispensing device has a housing with an aperture, wherein causing the scent dispensing device to dispense the plurality of first scents further includes causing the scent dispensing device to rotate the drum in order to align at least one chamber of the plurality of chambers with the aperture.

14. The system of claim 9, wherein causing a scent dispensing device to dispense the plurality of first scents further comprises sending the olfactory training exercise data to the scent dispensing device.

15. A system, comprising:

a plurality of chambers, wherein each chamber of the plurality of chambers includes a respective scent essence of a plurality of scent essences;

a processing circuitry; and a memory, the memory containing instructions that, when executed by the processing circuitry, configure the system to:

determine a plurality of first scents to be dispensed during a plurality of first olfactory training exercises indicated in olfactory training exercise data, wherein the olfactory training data further indicates a plurality of exercise trigger events, wherein each exercise trigger event of the plurality of exercise trigger events corresponds to a respective scent of the plurality of first scents; and dispense the plurality of first scents based on the olfactory training exercise data, wherein dispensing each scent of the plurality of first scents further comprises dispensing at least one scent essence of the plurality of scent essences via at least a portion of the plurality of chambers, wherein the plurality of first scents is dispensed such that the respective scent of the plurality of first scents is dispensed at a time defined with respect to the corresponding exercise trigger event of the plurality of exercise trigger events;

determine at least one training adjustment based on a performance of a user with respect to at least one scent category during the plurality of first olfactory training exercises, wherein the at least one training adjustment includes an adjustment to a number of different scents belonging to the at least one scent category to be dispensed during at least one second olfactory training exercise; and adjust training by performing the at least one second olfactory training exercise, wherein the at least one second olfactory training exercise is generated based on the plurality of first olfactory training exercises and the at least one training adjustment, wherein performing the at least one second olfactory training exercise includes dispensing at least one second scent via the scent dispensing device.

16. The system of claim 15, further comprising:

a plurality of actuators adapted to manipulate the plurality of scent essences disposed in the plurality of chambers;

wherein the system is further configured to:

drive application of pressure in at least one actuator of the plurality of actuators in order to induce emission of the at least one scent essence of the plurality of scent essences.

17. The system of claim 15, further comprising:

a drum having a body, wherein the plurality of chambers is disposed in the drum, wherein the body has a gear; and a housing having an aperture;

a cog wheel having teeth, wherein the teeth of the cog wheel mesh with the gear of the body;

a rotation motor adapted to rotate in contact with the cog wheel;

wherein the system is further configured to:

cause the drum to rotate in order to align at least one chamber of the plurality of chambers with the aperture by at least driving the rotation motor to rotate in contact with the cog wheel, wherein the cog wheel rotates in order to cause the gear of the body to rotate when the rotation motor rotates in contact with the cog wheel.

18. The system of claim 15, further comprising:

a plurality of actuators adapted to manipulate the plurality of scent essences disposed in the plurality of chambers;

a drum having a body, wherein the plurality of chambers is disposed in the drum, wherein the body has a gear; and a housing having an aperture;

a cog wheel having teeth, wherein the teeth of the cog wheel mesh with the gear of the body;

a rotation motor adapted to rotate in contact with the cog wheel;

wherein the system is further configured to:

rotate the drum in at least one rotation by at least driving the rotation motor to rotate in contact with the cog wheel, wherein the cog wheel rotates in order to cause the gear of the body to rotate when the rotation motor rotates in contact with the cog wheel, wherein rotating the drum at each rotation causes a chamber of the plurality of chambers to become aligned with the aperture of the housing; and drive application of pressure in at least one actuator of the plurality of actuators in order to induce emission of the at least one scent essence of the plurality of scent essences, wherein the application of pressure in each of the at least one actuator is performed during a respective rotation of the at least one rotation.

19. The system of claim 18, wherein the olfactory training exercise data further includes an order for the plurality of first olfactory training exercises, wherein the plurality of first scents is dispensed according to the order, wherein the application of pressure in each of the at least one actuator is performed during a respective olfactory training exercise of the plurality of olfactory training exercises based on the order.

* * * * *